United States Patent
Katsuura et al.

(10) Patent No.: US 6,423,849 B1
(45) Date of Patent: Jul. 23, 2002

(54) PROCESS OF PREPARING 5-(2-SUBSTITUTED-4-NITROPHENYL)-OXAZOLE, NOVEL OXAZOLE COMPOUND, AND PROCESS OF PREPARING THE SAME

(75) Inventors: Akio Katsuura; Azusa Yonezawa, both of Osaka; Keisuke Tsuzuki, Gifu; Kazumasa Hirata, Osaka, all of (JP)

(73) Assignee: The Nippon Synthetic Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 09/745,419

(22) Filed: Dec. 26, 2000

(30) Foreign Application Priority Data

Sep. 1, 2000 (JP) ........................................ 2000-264785
Sep. 1, 2000 (JP) ........................................ 2000-264786

(51) Int. Cl.$^7$ ............................................. C07D 263/32
(52) U.S. Cl. ...................................................... 548/235
(58) Field of Search ........................................... 548/235

(56) References Cited

U.S. PATENT DOCUMENTS 5,807,876 A * 9/1998 Armistead et al. .......... 514/374

FOREIGN PATENT DOCUMENTS

EP      WO 97 40028 A      10/1997

OTHER PUBLICATIONS

European Search Report dated Dec. 27, 2001.

M. Suzuki et al. "A facile Synthesis of 1–Oxy–1, 2–dihydroisoquinoline–3–carboxylate and 2–Pyridone–6–carboxylate Derivatives", No. 6, 1978, pp. 461–462.

* cited by examiner

Primary Examiner—Joseph K. McKane
Assistant Examiner—Sonya Wright
(74) Attorney, Agent, or Firm—Rader, Fishman & Grauer PLLC

(57) ABSTRACT

A 5-(2-substituted-4-nitrophenyl)-oxazole is prepared by decarboxylating a 5-(2-substituted-4-nitrophenyl)-4-oxazolecarboxylic acid in an aprotic amide solvent containing a protic compound. A 5-(2-substituted-4-nitrophenyl)-oxazolecarboxylic acid and a 5-(2-substituted-4-nitrophenyl)-carboalkoxyoxazole, which are novel compounds, are provided.

9 Claims, No Drawings

PROCESS OF PREPARING 5-(2-SUBSTITUTED-4-NITROPHENYL)-OXAZOLE, NOVEL OXAZOLE COMPOUND, AND PROCESS OF PREPARING THE SAME

BACKGROUND OF THE INVENTION

1. Field of the Invention

This invention relates to a process of preparing a 5-(2-substituted-4-nitrophenyl)-oxazole useful as a starting material of pharmaceuticals, such as an intermediate of a treating agent for hepatitis C and an anticancer agent; a novel oxazole compound, and a process of preparing the novel oxazole compound, particularly a manipulation for isolating the novel oxazole compound from a reaction mixture.

2. Description of the Related Art

A process of preparing a 5-(2-substituted-4-nitrophenyl)-oxazole is described in WO97/40028, in which 2-methoxy (or chloro)-4-nitrobenzaldehyde and tosylmethyl isocyanide are allowed to react.

Known oxazole compounds having a substituent include, for example, a 5-substituted-oxazole-4-carboxylic acid as disclosed in JP-A-Hei.4-134078. The substituents disclosed are substituted phenyl groups, and specific examples of the substituted phenyl groups disclosed are a p-toluyl group and a p-chlorophenyl group. The contemplated use of the oxazole compound in JP-A-Hei.4-134078 is an intermediate of antibiotics only.

The above-described process is disadvantageous in that the starting material is expensive and that the process involves by-products, such as toluenesulfinic acid, treatment of which incur high cost. Therefore it has been demanded to develop an industrially practical process which uses inexpensive starting materials and involves less production of by-products.

The inventors of the present invention had continued researches on novel oxazole compounds useful as a starting material of pharmaceuticals, such as an intermediate of a treating agent for hepatitis C and an anticancer agent, and a process for producing the same, particularly a process of isolating a desired compound from a reaction mixture efficiently.

The present inventors have found that decarboxylation of a 5-(2-substituted-4-nitrophenyl)-oxazolecarboxylic acid, which is a novel compound, provides a 5-(2-substituted-4-nitrophenyl)-oxazole without the above-described problems of the related art and thus completed the present invention.

They have also found that a 5-(2-substituted-4-nitrophenyl)-4-carboalkoxyoxazole, which is a novel compound, can be obtained in high purity through an industrially convenient operation by allowing a 2-substituted-4-nitrobenzoic acid and an isocyanoacetic acid or a derivative thereof to react in an organic solvent and adding water to the reaction mixture to precipitate crystals of the 5-(2-substituted-4-nitrophenyl)-4-carboalkoxyoxazole, which is collected by filtration.

SUMMARY OF THE INVENTION

An object of the invention is to provide a process of producing a 5-(2-substituted-4-nitrophenyl)-oxazole which is useful as a starting material of pharmaceuticals such as a treating agent of hepatitis C and an intermediate of an anticancer agent.

Another object of the invention is to provide a novel oxazole compound useful as a starting material of pharmaceuticals, such as an intermediate of an anticancer agent.

Still another object of the invention is to provide a process of producing the novel oxazole compound.

The present invention is especially achieved by the following means.

(1) A process of preparing a 5-(2-substituted-4-nitrophenyl)-oxazole comprising decarboxylating a 5-(2-substituted-4-nitrophenyl)-4-oxazolecarboxylic acid.

(2) The process according to (1), wherein the decarboxylation is carried out in an aprotic amide solvent containing a protic compound.

(3) The process according to (2), wherein the protic compound is water.

(4) The process according to any one of (1) to (3), wherein the decarboxylation is carried out at 70 to 140° C.

(5) The process according to any one of (1) to (4), wherein water is added to the reaction mixture after completion of the decarboxylation to precipitate the 5-(2-substituted-4-nitrophenyl)-oxazole at a high purity.

(6) The process according to any one of (1) to (5), wherein the 5-(2-substituted-4-nitrophenyl)-4-oxazolecarboxylic acid is a wet cake which is obtained by hydrolyzing a 5-(2-substituted-4-nitrophenyl)-4-carboalkoxyoxazole in an aqueous medium and filtering the reaction mixture.

(7) The process according to any one of (1) to (6), wherein the 5-(2-substituted-4-nitrophenyl)-oxazole is 5-(2-methoxy-4-nitrophenyl)-oxazole.

(8) The process according to any one of (1) to (6), wherein the 5-(2-substituted-4-nitrophenyl)-oxazole is 5-(2-chloro-4-nitrophenyl)-oxazole.

(9) The process according to any one of (1) to (8), wherein the 5-(2-substituted-4-nitrophenyl)-4-oxazolecarboxylic acid is a wet cake which is obtained by allowing a 2-substituted-4-nitrobenzoic acid or a derivative thereof and an isocyanoacetic acid or a derivative thereof in an organic solvent, adding water to the reaction mixture to precipitate crystals, collecting the crystals by filtration to obtain a 5-(2-substituted-4-nitrophenyl)-4-carboalkoxyoxazole, hydrolyzing the 5-(2-substituted-4-nitrophenyl)-4-carboalkoxyoxazole in an aqueous medium and filtering the reaction mixture.

(10) The process according to (9), wherein water, which is added to the reaction mixture after the reaction with a 2-substituted-4-nitrobenzoic acid or a derivative thereof and an isocyanoacetic acid or a derivative thereof in an organic solvent, is added in an amount of 0.5 to 4 parts by weight per part by weight of the organic solvent.

(11) An oxazole compound which is 5-(2-substituted-4-nitrophenyl)-4-oxazolecarboxylic acid.

(12) An oxazole compound which is 5-(2-substituted-4-nitrophenyl)-4-carboalkoxyoxazole

(13) A process of preparing a 5-(2-substituted-4-nitrophenyl)-oxazolecarboxylic acid comprising hydrolyzing a 5-(2-substituted-4-nitrophenyl)-carboalkoxyoxazole in an aqueous medium.

(14) A process of preparing a 5-(2-substituted-4-nitrophenyl)-4-carboalkoxyoxazole comprising allowing a 2-substituted-4-nitrobenzoic acid or a derivative thereof and an isocyanoacetic acid or a derivative thereof.

(15) The oxazole compound according to (11) or (12), wherein the substituent at the 2-position of the nitrophenyl moiety is an alkoxy group or a halogen atom.

DETAILED DESCRIPTION OF THE INVENTION

Examples of the above substituent (i.e., the substituent at the 2-position of the nitrophenyl moiety) include an alkoxy group (e.g., methoxy, ethoxy, propoxy, butoxy) and a halogen atom (e.g., chloro, bromo). Preferred examples thereof includes methoxy, ethoxy and chloro.

The 5-(2-substituted-4-nitrophenyl)-oxazole prepared by the process of the invention is represented by formula (I):

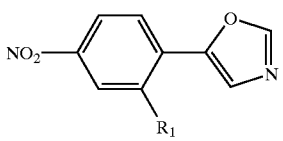

(I)

wherein $R_1$ represents a substituent.

Useful substituents as $R_1$ include an alkoxy group (e.g., methoxy, ethoxy, propoxy or butoxy) and a halogen atom (e.g., chlorine or bromine), with a methoxy group, an ethoxy group and a chlorine atom being preferred.

Specific examples of the oxazole compound represented by formula (I) are 5-(2-methoxy-4-nitrophenyl)-oxazole, 5-(2-ethoxy-4-nitrophenyl)-oxazole, and 5-(2-chloro-4-nitrophenyl)-oxazole.

The oxazole compound (I) can be produced by decarboxylating a 5-(2-substituted-4-nitrophenyl)-4-oxazolecarboxylic acid (hereinafter referred to as an oxazolecarboxylic acid). The reaction is preferably carried out in an aprotic amide solvent containing at least one protic compound.

Examples of the aprotic amide include N,N-dimethylformamide, N,N-dimethylacetamide, N,N-diethylformamide, N,N,N',N'-tetramethylurea, N-methylpyrrolidone, and N-formylpiperidine. From the standpoint of boiling point, yield, and cost, N,N-dimethylformamide is particularly preferred among them. Other solvents can be used in combination as long as is consistent with the scope of the invention.

Useful protic compounds include alcohols, carboxylic acids, phenols, and water. Water and alcohols are preferred from the viewpoint of yield, handling properties, ease of isolating a desired compound, and cost.

Examples of the alcohols include aliphatic ones, such as methanol, ethanol, n-propanol, isopropyl alcohol, n-butanol, isobutanol, sec-butanol, t-butanol, n-amyl alcohol, isoamyl alcohol, hexanol, and octanol; alicyclic ones, such as cyclopentanol and cyclohexanol; aromatic ones, such as benzyl alcohol and β-phenylethyl alcohol; heterocyclic ones, such as furfuryl alcohol; aliphatic polyhydric alcohols, such as ethylene glycol, propylene glycol, butanediol, hexanediol, glycerol, trimethylolethane, trimethylpropane, and neopentyl alcohol; and polyhydric alcohols having an ether bond, such as diethylene glycol, triethylene glycol, polyethylene glycol, dipropylene glycol, tripropylene glycol, and polypropylene glycol.

Examples of the carboxylic acids include formic acid, propionic acid, butyric acid, valeric acid, adipic acid, benzoic acid, and cyclohexanecarboxylic acid.

Examples of the phenols are phenol, cresol, xylenol, and o-chlorophenol.

While not limiting, the aprotic amide is used in an amount of 5 to 20 parts by weight, preferably 8 to 15 parts by weight, per part by weight of the oxazolecarboxylic acid.

The amount of the protic compound is not generally specified because it varies greatly according to the kind but usually ranges 0.01 to 20 parts, preferably 0.01 to 10 parts, by weight per part by weight of the oxazolecarboxylic acid.

The order of adding the oxazolecarboxylic acid, the aprotic amide, and the protic compound is arbitrary. They may be added all at once, or any one or two of them may be added in divided portions, or at least one of them may be added in a continuous manner.

The reaction is suitably carried out at 70 to 140° C., preferably 90 to 120° C. The reaction rate would be low at a temperature lower than 70° C., and the yield would be reduced at a temperature exceeding 140° C. The reaction usually completes in about 0.5 to 10 hours.

After completion of the reaction, the aprotic amide and the protic compound are removed from the reaction mixture through known means, for example, distillation under reduced pressure. The residue or concentrate, which still contains slight impurities, is further purified by recrystallization, washing, and the like to obtain the desired compound.

In an alternative method for isolating the desired compound, which is a highly preferred embodiment of the present invention, water is added to the reaction mixture, whereby the compound of formula (I) is easily precipitated with high purity. This water addition method also serves for purification of the product. Water is added in an amount of 0.1 to 1.5 parts by weight, preferably 0.5 to 1 part by weight, per part by weight of the aprotic amide.

The present invention also provides novel oxazole compounds represented by formula (II), which is 5-(2-substituted-nitrophenyl)-4-carboalkoxyoxazole (when $R_2$ is an alkyl group) or 5-(2-substituted-4nitrophenyl)-4-oxazolecarboxylic acid (when $R_2$ is a hydrogen atom):

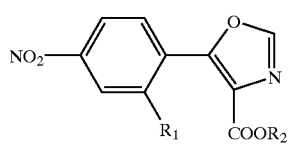

(II)

wherein $R_1$ represents an alkoxy group or a halogen atom; and $R_2$ represents a hydrogen atom or an alkyl group.

In formula (II), the alkoxy group as represented by $R_1$ includes methoxy, ethoxy, propoxy, and butoxy, and the halogen atom as $R_1$ includes chlorine and bromine. $R_2$ is preferably methoxy, ethoxy or chlorine. The alkyl group as represented by $R_2$ includes methyl and ethyl.

Specific examples of the compounds (II) include 5-(2-substituted-nitrophenyl)-4-carboalkoxyoxazoles ($R_2$: alkyl), such as 5-(2-methoxy-4-nitrophenyl)-4-carboethoxyoxazole, 5-(2-chloro-4-nitrophenyl)-4-carboethoxyoxazole, 5-(2-methoxy-4-nitrophenyl)-4-carbomethoxyoxazole, 5-(2-chloro-4-nitrophenyl)-4-carbomethoxyoxazole; and 5-(2-substituted-nitrophenyl)-4-oxazolecarboxylic acids ($R_2$: H), such as 5-(2-methoxy-4-nitrophenyl)-4-oxazolecarboxylic acid and 5-(2-chloro-4-nitrophenyl)-4-oxazolecarboxylic acid.

The 5-(2-substituted-nitrophenyl)-4-carboalkoxyoxazole (II; $R_2$: alkyl) can easily be prepared by the reaction between a 2-substituted-4-nitrobenzoic acid represented by formula (III):

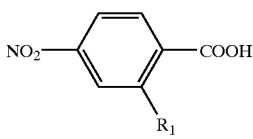

wherein $R_1$ is as defined above, or a derivative thereof and an isocyanoacetic acid or a derivative thereof represented by formula (IV):

wherein $R_2$ is as defined above.

The reaction is usually conducted between a chloride of the benzoic acid (III) and an isocyanoacetate (III) in an organic solvent in the presence of a base. The reaction is usually carried out at 0 to 50° C. for 2 to 4 hours.

The base includes organic bases, such as triethylamine and tributylamine; and inorganic bases, such as alcoholates (e.g., potassium t-butoxide) and alkali metal hydrides (e.g., lithium hydride); with triethylamine being preferred. The base is used in an amount of 1 mol or more, preferably 1.5 to 6 mol, per mole of the isocyanoacetate.

The solvent includes amides, such as N,N-dimethylformamide and N,N-dimethylacetamide; ethers, such as tetrahydrofuran and diethyl ether; and halogenated hydrocarbons, such as dichloromethane and chloroform. These solvents can be used either individually or as a mixture thereof. The amount of the solvent to be used is usually about 3 to 10 times the weight of the benzoic acid (or a derivative thereof).

The product is isolated from the reaction mixture and purified in a usual manner by, for example, concentration, distillation and crystallization.

In a highly preferred embodiment, the product is isolated by removing insoluble matter from the reaction mixture and adding water to the mother liquor to precipitate the product. Water is added in an amount of 0.5 to 4 parts by weight per part by weight of the organic solvent. Addition of less than 0.5 part of water has poor effect in causing precipitation, and addition of more than 4 parts of water tends to affect the operational efficiency. The product thus isolated has sufficient purity but, if desired, can be subjected to further purification procedures.

The oxazolecarboxylic acid (II, $R_2$: H) can be obtained by hydrolysis of the carboalkoxyoxazole (II; $R_2$: alkyl). Hydrolysis of the carboalkoxyoxazole (II) is usually carried out in water or a water-containing alcohol in the presence of an inorganic base, such as sodium hydroxide or potassium hydroxide, at a temperature of from room temperature to the refluxing temperature for 1 to 5 hours.

The inorganic base is used in an amount of 1 mol or more, preferably 1.0 to 2.5 mol, still preferably 1.2 to 2.5 mol, per mole of the carboalkoxyoxazole (II).

In carrying out the preparation of the compound (II), the order of adding the reactants solvent, etc. is arbitrary. They can be added all at once or in divided portions, either continuously or dropwise. Addition of all the materials at once is advantageous.

Since the oxazolecarboxylic acid is obtained in the form of its salt, which is dissolved in the reaction mixture, it is neutralized with an acid, e.g., sulfuric acid or hydrochloric acid, and the precipitate is collected by filtration for use in the subsequent decarboxylation step. Where decarboxylation is effected with water or an alcohol as a protic compound, it is industrially advantageous to use the oxazolecarboxylic acid as collected by filtration in wet cake form. The water content of the wet cake is to be adjusted appropriately, taking it into consideration that the amount of water (protic compound) in the decarboxylation reaction system is usually in the range of from 0.01 to 20 parts by weight per part by weight of the oxazolecarboxylic acid.

The invention will now be illustrated in greater detail with reference to Examples, but it should be understood that the invention is not limited thereto. Unless otherwise noted, all the percents and parts are by weight.

EXAMPLE 1

Starting Material Preparation 1 (Synthesis of 5-(2-methoxy-4-nitrophenyl)-4-carboethoxyoxazole)

In 80 ml of N,N-dimethylformamide (hereinafter abbreviated as DMF) was dissolved 17.7 g (0.09 mol) of 2-methoxy-4-nitrobenzoic acid, and 11.9 g (0.09 mol) of thionyl chloride was added thereto dropwise over 1 hour to prepare 2-methoxy-4-nitrobenzoic acid chloride. Separately, 30.4 g (0.3 mol) of triethylamine and 11.3 g (0.1 mol) of ethyl isocyanoacetate were dissolved in 50 ml of DMF, and the solution was kept at 0° C. The above prepared acid chloride solution was added thereto dropwise, and the mixture was allowed to react for 4 hours.

After completion of the reaction, the reaction mixture was filtered, the filtrate concentrated, and the concentrate purified by silica gel column chromatography to give 17.2 g (0.059 mol; 65.3% based on the 2-methoxy-4-nitrobenzoic acid) of the title compound.

Mp: 106–107° C.

MS (m/z): 292 ($M^+$)

$^1$H-NMR (CDCl$_3$; ppm): 1.32 (t, 3H), 3.94 (s, 3H), 4.34 (q, 2H), 7.69 (d, 1H), 7.85 (d, 1H), 7.94 (dd, 1H), 8.01 (s, 1H)

$^{13}$C-NMR (CDCl$_3$; ppm): 14.2, 56.3, 61.4, 106.3, 115.3, 122.5, 130.2, 132.1, 150.1, 150.3, 150.6, 158.0, 161.3

Starting Material Preparation 2 (Synthesis of 5-(2-methoxy-4-nitrophenyl)-4-oxazolecarboxylic acid)

To 780 ml of water were added 15.6 g (0.053 mol) of the 5-(2-methoxy-4-nitrophenyl)-4-carboethoxyoxazole prepared in (1) above and 24.0 g (0.107 mol) of a 25% aqueous solution of potassium hydroxide, and the mixture was allowed to react at 80° C. for 1 hour. After cooling to room temperature, the reaction mixture was adjusted to pH 2 with 30% sulfuric acid. The crystals thus precipitated were collected by filtration to obtain the title compound as a wet cake weighing 41.3 g and having a water content of 68%. That is, the yield of the compound was 13.2 g (0.05 mol, 93.9% based on the 5-(2-methoxy-4-nitrophenyl)-4-carboethoxyoxazole).

Mp: 215° C. (decomp.)

MS (m/z): 264

$^1$H-NMR (DMSO-d$_6$, ppm): 3.35 (b, 1H), 3.92 (s, 3H), 7.79 (d, 1H), 7.91 (s, 1H), 7.94 (d, 1H), 8.63 (s, 1H)

$^{13}$C-NMP (DMSO-d$_6$, ppm): 56.5, 106.6, 115.2, 122.7, 130.5, 132.3, 149.1, 149.7, 152.1, 157.7, 162.5

Preparation of Target Commpound of the Present Invention (5-(2-methoxy-4-nitrophenyl)-oxazole)

In 130 g of DMF was dissolved 38.1 g of the wet cake obtained in (2) above (5-(2-methoxy-4-nitrophenyl)-4-oxazolecarboxylic acid: 12.2 g (0.046 mol); water: 25.9 g), and the solution was heated at 100° C. for 6 hours to perform decarboxylation. After cooling, 71 g of water was added to the reaction mixture followed by stirring for 30 minutes. The precipitate was collected by filtration to give 7.6 g of crystals. The crystals were identified to be the title compound by GC-MS analysis (m/z=220) and $^1$H-NMR analysis. The yield was 75% based on the 5-(2-methoxy-4-nitrophenyl)-4-oxazolecarboxylic acid.

Purity: 99.3%

Mp: 151° C.

EXAMPLE 2

Preparation of 5-(2-methoxy-4-nitrophenyl)-oxazole:

5-(2-Methoxy-4-nitrophenyl)-4-oxazolecarboxylic acid was prepared in the same manner as in Example 1-(1) and (2), and the resulting wet cake was dried. The dried product (13.2 g, 0.05 mol) was dissolved in 130 g of DMF. Water (66 g) was added thereto, and the solution was heated at 90° C. for 9 hours for decarboxylation. After cooling, 31 g of water was added to the reaction mixture. The mixture was stirred for 30 minutes, and the precipitate was collected by filtration to give 7.6 g (76% based on the 5-(2-methoxy-4-nitrophenyl)-4-oxazolecarboxylic acid) of the title compound as crystals.

Purity: 99.4%

Mp: 151° C.

EXAMPLE 3

In 130 g of DMF was dissolved 13.2 g (0.05 mol) of dry 5-(2-methoxy-4-nitrophenyl)-4-oxazolecarboxylic acid, and 1.3 g of water was added thereto. The mixture was heated at 140° C. for 4 hours to conduct decarboxylation. DMF was removed, and the residue was purified by column chromatography to yield 6.8 g of yellow crystals. The crystals were identified to be 5-(2-methoxy-4-nitrophenyl)-oxazole by GC-MS analysis (m/z=220) and $^1$H-NMR analysis. The yield was 61.8% based on the 5-(2-methoxy-4-nitrophenyl)-4-oxazolecarboxylic acid.

Purity: 99.4%

Mp: 151° C.

EXAMPLE 4

Starting Material Preparation 1 Synthesis of 5-(2-chloro-4-nitrophenyl)-4-carboethoxyoxazole The procedures of Example 1-(1) were followed, except for starting with 18.1 g (0.09 mol) of 2-chloro-4-nitrobenzoic acid in place of the 2-methoxy-4-nitrobenzoic acid, to afford 17.4 g (0.059 mol, 65.2% based on the 2-chloro-4-nitrobenzoic acid) of the title compound.

Mp: 140–141° C.

MS (m/z): 261 (M–35.5)

$^1$H-NMR (CDCl$_3$, ppm): 1.31 (t, 3H), 4.34 (q, 2H), 7.79 (d, 1H), 8.09 (s, 1H), 8.24 (dd, 1H), 8.40 (d, 1H)

$^{13}$C-NMR (CDCl$_3$, ppm): 14.1, 61.8, 121.4, 125.1, 130.8, 132.7, 133.3, 135.7, 149.2, 150.5, 151.1, 160.7

The procedures of Example 1 (Starting Material Preparation 2) were followed, except for replacing the 5-(2-chloro-4-nitrophenyl)-4-carboethoxyoxazole with 15.13 g (0.051 mol) of 5-(2-chloro-4-nitrophenyl)-4-carboethoxyoxazole, to obtain 12.53 g (0.046 mol, 91.5% based on the 5-(2-chloro-4-nitrophenyl)-4-carboethoxyoxazole) of the title compound.

Mp: 181° C. (decomp.)

MS (m/z): 233 (M–35.3)

$^1$H-NMR (DMSO-d$_6$, ppm): 3.34 (b, 1H), 7.99 (d, 2H), 8.31 (dd, 1H), 8.48 (s, 1H), 8.72 (s, 1H)

$^{13}$C-NMR (CDCl$_3$, ppm): 122.2, 124.7, 130.9, 133.1, 134.1, 134.4 149.3, 152.8, 161.9

Preparation of 5-(2-chloro-4-nitrophenyl)-oxazole

The carboethoxyoxazole compound obtained in (1) above was hydrolyzed in the same manner as in Example 1-(2) to prepare 5-(2-chloro-4-nitrophenyl)-4-oxazolecarboxylic acid, which was then allowed to react in the same manner as in Example 1-(3) to obtain the title compound in a yield of 72% based on the oxazolecarboxylic acid. The identification of the product was carried out by GC-MS (m/z=224) and $^1$H-NMR analysis. Starting Material Preparation 2 (Synthesis of 5-(2-chloro-4-nitrophenyl)-4-oxazolecarboxylic acid):

EXAMPLE 5

Preparation of 5-(2-methoxy-4-nitrophenyl)-4-carboethoxyoxazole

In 19 g of DMF were dissolved 9.4 g (0.093 mol) of triethylamine and 5.3 g (0.046 mol) of ethyl isocyanoacetate. Separately, 9.9 g (0.046 mol) of 2-methoxy-4-nitrobenzoic acid chloride was dissolved in 23 g of DMF, and the solution was kept at 25° C. To the solution was added dropwise the above-prepared DMF solution of ethyl isocyanoacetate over a period of 5 hours, followed by aging for 1 hour.

After completion of the reaction, the triethylamine hydrochloride was separated by filtration and washed with 20 g of DMF. The washing and the filtrate were combined, and 120 g of water (corresponding to 1.9 parts per part of DMF) was added to precipitate crystals. The crystals were collected by filtration and dried to give 10.8 g (0.037 mol, 80.4% based on the acid chloride) of the title compound. The purity was 97.0%.

Mp: 106–107° C.

MS (m/z): 292 (M$^+$)

$^1$H-NMR (CDCl$_3$, ppm): 1.32 (t, 3H), 3.94 (s, 3H), 4.34 (q, 2H), 7.69 (d, 1H), 7.85 (d, 1H), 7.94 (dd, 1H), 8.01 (s, 1H)

$^{13}$C-NMR (CDCl$_3$, ppm): 14.2, 56.3, 61.4, 106.3, 115.3, 122.5, 130.2, 132.1, 150.1, 150.3, 150.6, 158.0, 161.3

EXAMPLE 6

Preparation of 5-(2-chloro-4-nitrophenyl)-4-carboethoxyoxazole

The procedures of Example 5 were followed, except for replacing the 2-methoxy-4-nitrobenzoic acid chloride with 10.1 g (0.046 mol) of 2-chloro-4-nitrobenzoic acid chloride, to furnish 10.8 g (0.036 mol, 79.2% based on the acid chloride) of the title compound. The purity of the product was 96.5%.

Mp: 140–141° C.

MS (m/z): 261 (M–35.5)

$^1$H-NMR (CDCl$_3$, ppm): 1.31 (t, 3H), 4.34 (q, 2H), 7.79 (d, 1H), 8.09 (s, 1H), 8.24 (dd, 1H), 8.40 (d, 1H)

$^{13}$C-NMR (CDCl$_3$, ppm): 14.1, 61.8, 121.4, 125.1, 130.8, 132.7, 133.3, 135.7, 149.2, 150.5, 151.1, 160.7

EXAMPLE 7

Preparation of 5-(2-methoxy-4-nitrophenyl)-4-carbomethoxyoxazole

The procedures of Example 5 were followed, except for replacing the ethyl isocyanoacetate with 4.6 g (0.046 mol) of methyl isocyanoacetate, to furnish 10.3 g (0.037 mol, 80.6% based on the acid chloride) of the title compound. The purity of the product was 97.2%.

Mp: 186–187° C.

MS (m/z): 278 (M$^+$)

$^1$H-NMR (CDCl$_3$, ppm): 3.87 (s, 3H), 3.49 (s, 3H), 7.69 (d, 1H), 7.85 (d, 1H), 7.96 (dd, 1H), 8.01 (s, 1H)

$^{13}$H-NMR (CDCl$_3$, ppm): 52.3, 56.3, 61.4, 106.4, 115.4, 122.3, 130.0, 132.0, 150.2, 150.4, 158.0, 161.7

EXAMPLE 8

Preparation of 5-(2-methoxy-4-nitrophenyl)-4-oxazolecarboxylic acid

In 50 ml of methanol were added 15.0 g (0.051 mol) of 5-(2-methoxy-4-nitrophenyl)-4-carboethoxyoxazole obtained in Example 1-(1) and 9.8 g (0.061 mol) of a 25% aqueous solution of sodium hydroxide, and the mixture was allowed to react at 40° C. for 4 hours. The reaction mixture was filtered to collect sodium 5-(2-methoxy-4-nitrophenyl)-4-oxazolecarboxylate as a wet cake, which was dissolved in 1000 ml of water and adjusted to pH 2 with 35% hydrochloric acid. The crystals thus precipitated were collected by filtration to obtain 12.2 g (0.046 mol, 90.2% based on the 5-(2-methoxy-4-nitrophenyl)-4-carboethoxyoxazole) of the title compound.

Mp: 215° C. (decomp.)

MS (m/z): 264 (M$^+$)

$^1$H-NMR (DMSO-d$_6$, ppm); 3.35 (b, 1H), 3.92 (s, 3H), 7.79 (d, 1H), 7.91 (s, 1H), 7.94 (d, 1H), 8.63 (s, 1H)

$^{13}$C-NMR (DMSO-d$_6$, ppm): 56.5, 106.6. 115.2, 122.7, 130.5, 132.3, 149.1, 149.7, 152.1, 157.7, 162.5

EXAMPLE 9

Preparation of 5-(2-methoxy-4-nitrophenyl)-4-carbomethoxyoxazole

The procedures of Example 1-(1) were followed, except for replacing the ethyl isocyanoacetate with 9.9 g (0.1 mol) of methyl isocyanoacetate, to obtain 15.4 g (0.055 mol 61.5% based on the 2-methoxy-4-nitrobenzoic acid) of the title compound.

Mp: 186–187° C.

MS (m/z) : 278 (M$^+$)

$^1$H-NMR (CDCl$_3$, ppm): 3.87 (s, 3H), 3.49 (s, 3H), 7.69 (d, 1H), 7.85 (d, 1H), 7.96 (dd, 1H), 8.01 (s, 1H)

$^{13}$H-NMR (CDCl$_3$, ppm): 52.3, 56.3, 61.4, 106.4, 115.4, 122.3, 130.0, 132.0, 150.2, 150.4, 158.0, 161.7

EXAMPLE 10

Preparation of 5-(2-chloro-4-nitrophenyl)-4-carbomethoxyoxazole

The procedures of Example 1-(l) were followed, except for replacing the 2-methoxy-4-nitrobenzoic acid with 18.1 g (0.09 g) of 2-chloro-4-nitrobenzoic acid and replacing the ethyl isocyanoacetate with 9.9 g (0.1 mol) of methyl isocyanoacetate, to give 16.2 g (0.057 mol, 63.7% based on the 2-chloro-4-nitrobenzoic acid) of the title compound.

Mp: 121–122° C.

MS (m/z): 247 (M–35.5)

$^1$H-NMR (CDCl$_3$, ppm): 3.88 (s, 3H), 7.77 (d, 1H), 8.07 (s, 1H), 8.24 (dd, 1H), 8.40 (d, 1H)

$^{13}$C-NMR (CDCl$_3$, ppm): 52.3, 121.3, 125.0, 130.3, 132.3, 133.1, 135.4, 149.0, 150.5, 151.0, 160.9

According to the present invention, a 5-(2-substituted-4-nitrophenyl)-oxazole useful as a starting material of pharmaceuticals, such as an intermediate of a treating agent for hepatitis C and an anticancer agent, can be produced with industrial advantages by decarboxylation of a 5-(2-substituted-4-nitrophenyl)-4-oxazolecarboxylic acid.

The present invention provides novel oxazole compounds, e.g., a 5-(2-substituted-4-nitrophenyl)-4-carboalkoxyoxazole and a 5-(2-substituted-4-nitrophenyl)-4-oxazolecarboxylic acid, which are useful as a starting material of pharmaceuticals, such as an intermediate of a treating agent for hepatitis C and an anticancer agent. The 5-(2-substituted-4-nitrophenyl)-4-carboalkoxyoxazole can be isolated efficiently by adding water to the reaction mixture.

While the invention has been described in detail and with reference to specific examples thereof, it will be apparent to one skilled in the art that various changes and modifications can be made therein without departing from the spirit and scope thereof.

The entire disclosure of each and every foreign patent application from which the benefit of foreign priority has been claimed in the present application is incorporated herein by reference, as if fully set forth.

What is claimed is:

1. A process of preparing a 5-(2-substituted-4-nitrophenyl)-oxazole, which comprises decarboxylating a 5-(2-substituted-4-nitrophenyl)-4-oxazolecarboxylic acid;

wherein the decarboxylation is carried out in an aprotic amide solvent containing a protic compound.

2. The process according to claim 1, wherein said protic compound is water.

3. The process according to claim 1, wherein the decarboxylation is carried out at 70 to 140° C.

4. The process according to claim 1, wherein water is added to the reaction mixture after completion of the decarboxylation to precipitate said 5-(2-substituted-4-nitrophenyl)-oxazole at a high purity.

5. The process according to claim 1, wherein said 5-(2-substituted-4-nitrophenyl)-4-oxazolecarboxylic acid is a wet cake which is obtained by hydrolyzing a 5-(2-substituted-4-nitrophenyl)-carboalkoxyoxazole in an aqueous medium and filtering the reaction mixture.

6. The process according to claim 1, wherein said 5-(2-substituted-4-nitrophenyl)-oxazole is 5-(2-methoxy-4-nitrophenyl)-oxazole.

7. The process according to claim 1, wherein said 5-(2-substituted-4-nitrophenyl)-oxazole is 5-(2-chloro-4-nitrophenyl)-oxazole.

8. The process according to claim 1, wherein said 5-(2-substituted-4-nitrophenyl)-4-oxazolecarboxylic acid is a wet cake which is obtained by allowing a 2-substituted-4-nitrobenzoic acid or a derivative thereof and an isocyanoacetic acid or a derivative thereof in an organic solvent, adding water to the reaction mixture to precipitate crystals, collecting the crystals by filtration to obtain a 5-(2-substituted-4-nitrophenyl)-4-carboalkoxyoxazole, hydrolyzing the 5-(2-substituted-4-nitrophenyl)-carboalkoxyoxazole in an aqueous medium and filtering the reaction mixture.

9. The process according to claim 8, wherein water is added in an amount of 0.5 to 4 parts by weight per part by weight of said organic solvent.

* * * * *